(12) United States Patent
Boronyak et al.

(10) Patent No.: US 9,259,261 B2
(45) Date of Patent: Feb. 16, 2016

(54) ABLATION CATHETER HAVING TEMPERATURE-CONTROLLED ANCHOR AND RELATED METHODS

(71) Applicant: Vanderbilt University, Nashville, TN (US)

(72) Inventors: Steven M. Boronyak, Nashville, TN (US); William David Merryman, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 206 days.

(21) Appl. No.: 13/861,884

(22) Filed: Apr. 12, 2013

(65) Prior Publication Data

US 2013/0296851 A1  Nov. 7, 2013

Related U.S. Application Data

(63) Continuation-in-part of application No. 13/384,148, filed on Jun. 15, 2012.

(60) Provisional application No. 61/623,105, filed on Apr. 12, 2012, provisional application No. 61/656,678, filed on Jun. 7, 2012.

(51) Int. Cl.
  *A61B 18/18*   (2006.01)
  *A61B 18/00*   (2006.01)
  *A61B 18/14*   (2006.01)
  *A61B 18/02*   (2006.01)
  *A61B 18/12*   (2006.01)

(52) U.S. Cl.
  CPC ............. *A61B 18/00* (2013.01); *A61B 18/1492* (2013.01); *A61B 2018/00023* (2013.01); *A61B 2018/00273* (2013.01); *A61B 2018/00791* (2013.01); *A61B 2018/0212* (2013.01); *A61B 2018/1226* (2013.01)

(58) Field of Classification Search
  CPC ................. A61B 18/18; A61B 2018/00005; A61B 2018/0022; A61B 2018/00273; A61B 2018/00285; A61B 18/00; A61B 18/1492; A61B 2018/0212; A61B 2018/1226
  USPC ............................................. 606/40, 41, 49
  See application file for complete search history.

(56) References Cited

U.S. PATENT DOCUMENTS

2005/0288730 A1* 12/2005 Deem et al. ............... 607/42
2011/0082453 A1*  4/2011 Fischer ............... A61B 18/02
                                                        606/21

OTHER PUBLICATIONS

U.S. Appl. No. 13/384,148—Claims.*

* cited by examiner

*Primary Examiner* — Theodore Stigell
*Assistant Examiner* — Michael Carey
(74) *Attorney, Agent, or Firm* — Tarolli, Sundheim, Covell & Tummino LLP

(57) ABSTRACT

One aspect of the present disclosure includes a catheter. The catheter includes a catheter body having a temperature-controlled anchor element thereon that is configured to attach the catheter body to tissue by forming a congealed adherence layer between the anchor element and the tissue. The catheter also includes an ablation element connected to the catheter body. The ablation element is axially spaced apart from the anchor element. The ablation element is configured to ablate tissue when the anchor element is attached to the tissue.

20 Claims, 8 Drawing Sheets

ABLATION CATHETER HAVING TEMPERATURE-CONTROLLED ANCHOR AND RELATED METHODS

RELATED APPLICATIONS

This is a continuation-in-part of U.S. patent application Ser. No. 13/384,148, filed Jun. 15, 2012 (U.S. Patent Publication No. 2013/0030424 A1). This application also claims the benefit of U.S. Provisional Patent Application Ser. Nos. 61/623,105, filed Apr. 12, 2012, and 61/656,678, filed Jun. 7, 2012. The entirety of each of the aforementioned applications is hereby incorporated by reference for all purposes.

TECHNICAL FIELD

The present disclosure relates generally to catheters, and more particularly to an ablation catheter having a temperature-controlled anchor element and related methods of use.

BACKGROUND

The mitral valve is a complex structure located between the left atrium and ventricle of the mammalian heart. During systole, large pressures (e.g., greater than 120 mmHg) are imposed on the closed mitral valve. The mitral valve leaflets resist these pressures to prevent mitral regurgitation, which can cause serious cardiac complications. The mitral valve includes two leaflets (anterior and posterior) whose free edges are tethered to the wall of the left ventricle at the papillary muscles via the chordae tendinae. The basal edges of the leaflets are attached to the left ventricle via a fibrous annular ring. The anterior leaflet is a single continuous membrane, and the posterior leaflet is made up of three scallops with the central scallop being the largest.

Although there are multiple components of the mitral valve complex that can lead to dysfunction, a loss of structural integrity of the mitral valve leaflets to withstand systolic pressure can be detrimental to mitral valve performance. A specific mitral valve syndrome called mitral valve prolapse occurs when the leaflets billow back into the left atrium during systole, typically resulting in compromised mitral valve and cardiac function. Cardiologic hallmarks of mitral valve prolapse include superior displacement, such as more than 2 mm, of one or both of the leaflets into the left atrium.

Clinically, there are two distinct patient groups with mitral valve prolapse. The first group is typically younger females, and the majority of this group does not require intervention. The second group is older males with moderate to severe mitral regurgitation and thickening leaflets. Histological analysis of autopsied mitral valve prolapse leaflets from this second patient group typically reveals disrupted and/or fragmented collagen architecture with enhanced quantity of proteoglycans. This disrupted architecture is called myxomatous mitral valve disease. Because of the disrupted architecture of the myxomatous mitral valve leaflets, collagen fibers are unable to provide the needed structural integrity to appose left ventricle pressure during systole, and the leaflet(s) displaces into the atrium, prohibiting closure and leading to mitral regurgitation.

Standard treatments for myxomatous mitral valve disease are surgical repair or replacement. Both repair and replacement of the mitral valve are expensive, potentially invasive procedures with substantial recovery times. Percutaneous edge-to-edge repair procedures can be used in some cases of myxomatous mitral valve disease, which avoids open-chest surgery and reduces hospital stay and recovery time. However, the current mode of edge-to-edge repair has a significant detractor in that it can form a double-orifice mitral valve, and the long-term fluid mechanics and left ventricle remodeling of this flow pattern are not well-understood. Moreover, if the degree of myxomatous degeneration is high, the edge-to-edge technique may not be suitable. Edge-to-edge repairs are also not suitable for many patients, including those with ischemic mitral regurgitation, recurrent mitral regurgitation after complex mitral valve repair, or mitral regurgitation associated with papillary muscle displacement. On the other hand, mitral valve replacement surgeries typically involve open-heart surgery, which can be problematic, especially in an older patient population.

SUMMARY

In one aspect, the present disclosure includes a catheter. The catheter includes a catheter body having a temperature-controlled anchor element thereon that is configured to attach the catheter body to tissue by forming a congealed adherence layer between the anchor element and the tissue. The catheter also includes an ablation element connected to the catheter body. The ablation element is axially spaced apart from the anchor element. The ablation element is configured to ablate tissue when the anchor element is attached to the tissue.

In another aspect, the present disclosure includes a method for ablating tissue. One step of the method includes providing a catheter body having a temperature-controlled anchor element thereon adjacent body tissue while cooling the anchor element to a temperature sufficient to form a congealed adherence layer between the anchor element and the tissue to attach the catheter body to the tissue. Next, an ablation element that is connected to the catheter is positioned adjacent the tissue. The ablation element is axially spaced apart from the anchor element. The tissue is then ablated when the anchor element is attached to the tissue.

In another aspect, the present disclosure can include a catheter comprising a catheter body. The catheter body can have first and second temperature-controlled anchor elements thereon. Each of the first and second anchor elements can be configured to attach the catheter body to tissue by forming a congealed adherence layer between the first and second anchor elements and the tissue. The catheter body can also include an ablation element connected thereto and disposed between the first and second anchor elements. The ablation element can be configured to ablate tissue when the first and second anchor elements are attached to the tissue. Each of the first anchor element, the second anchor element, and the ablation element can be axially spaced apart from one another.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

Figure 1A:
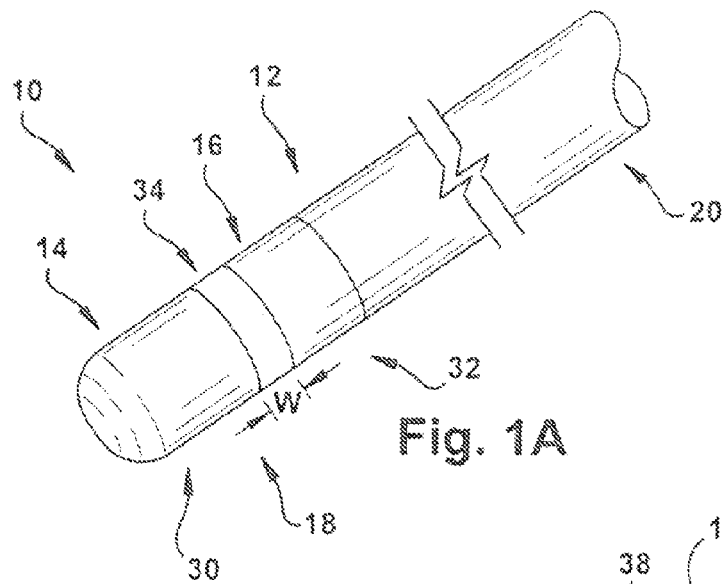
FIG. 1A is a perspective view of a catheter for ablating tissue constructed in accordance with one aspect of the present disclosure.

Unless otherwise defined, all technical terms used herein have the same meaning as commonly understood by one of ordinary skill in the art to which the present disclosure pertains.

In the context of the present disclosure, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, phrases such as "between X and Y" and "between about X and Y" can be interpreted to include X and Y.

As used herein, phrases such as "between about X and Y" can mean "between about X and about Y."

As used herein, phrases such as "from about X to Y" can mean "from about X to about Y."

It will be understood that when an element is referred to as being "on," "attached" to "connected" to "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms can encompass different orientations of the apparatus in use or operation in addition to the orientation depicted in the figures. For example, if the apparatus in the figures is inverted, elements described as "under" or "beneath" other elements or features would then be oriented "over" the other elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or figures unless specifically indicated otherwise.

As used herein, the term "subject" can refer to any warm-blooded organism including, but not limited to, human beings, pigs, rats, mice, dogs, goats, sheep, horses, monkeys, apes, rabbits, cattle, etc.

As used herein, the term "tissue" can refer to any biological tissue, such as organs, tendons, muscle, bone, skin, etc. In one example, the term "tissue" can include cardiac tissue. Cardiac tissue can include, in some instances, epicardium, myocardium, endocardium, or a portion thereof. In other instances, cardiac tissue can include a heart valve, such as the mitral valve, the tricuspid valve, an atrioventricular valve, and a semilunar valve, including leaflets thereof, as well as other structure associated with the heart valve, such as the annulus, tendinae chordate, etc.

The present disclosure includes reference to block diagrams and/or flowchart illustrations of methods, apparatus (systems) and/or computer program products according to certain aspects of the disclosure. It is understood that each block of the block diagrams and/or flowchart illustrations, and combinations of blocks in the block diagrams and/or flowchart illustrations, can be implemented by computer program instructions. These computer program instructions may be provided to a processor of a general purpose computer, special purpose computer, and/or other programmable data processing apparatus to produce a machine, such that the instructions, which execute via the processor of the computer and/or other programmable data processing apparatus, create means for implementing the functions/acts specified in the block diagrams and/or flowchart block or blocks.

These computer program instructions may also be stored in a computer-readable memory that can direct a computer or other programmable data processing apparatus to function in a particular manner, such that the instructions stored in the computer-readable memory produce an article of manufacture including instructions, which implement the function/act specified in the block diagrams and/or flowchart block or blocks.

The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions/acts specified in the block diagrams and/or flowchart block or blocks.

Accordingly, the present disclosure may be embodied in hardware and/or in software (including firmware, resident software, micro-code, etc.). Furthermore, aspects of the present disclosure may take the form of a computer program product on a computer-usable or computer-readable storage medium having computer-usable or computer-readable program code embodied in the medium for use by or in connection with an instruction execution system. A computer-usable or computer-readable medium may be any medium that can contain or store the program for use by or in connection with the instruction or execution of a system, apparatus, or device.

The computer-usable or computer-readable medium may be, for example but not limited to, an electronic, magnetic, optical, electromagnetic, infrared, or semiconductor system, apparatus or device. More specific examples (a non-exhaustive list) of the computer-readable medium can include the following: a portable computer diskette; a random access memory; a read-only memory; an erasable programmable read-only memory (or Flash memory); and a portable compact disc read-only memory.

Figure 1B:
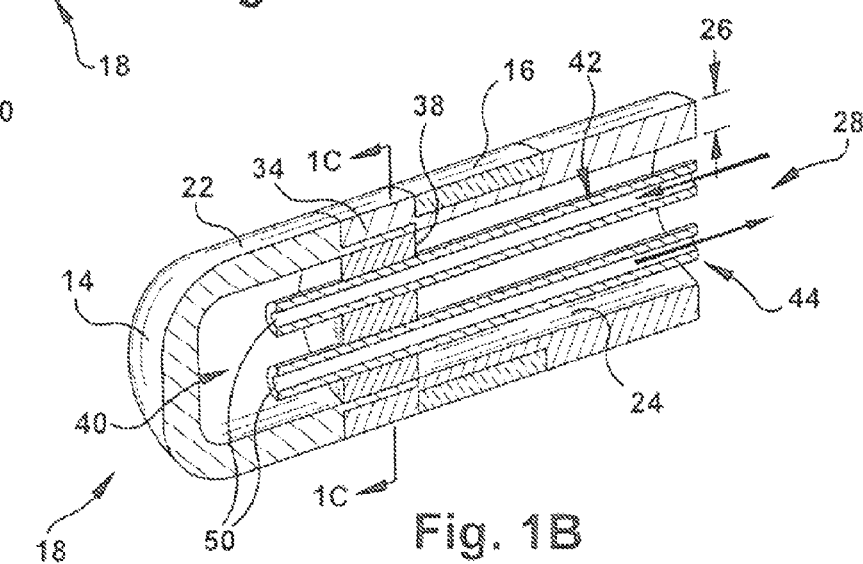
FIG. 1B is a magnified cut-away view of a distal end of the catheter in FIG. 1A.
Figure 1C:
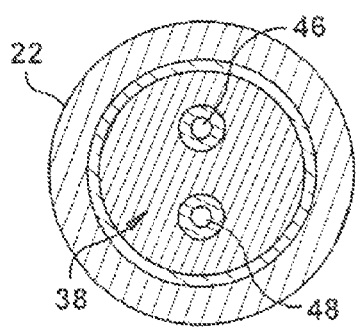
FIG. 1C is a cross-sectional view taken along Line 1C-1C in FIG. 1B.

The present disclosure relates generally to catheters, and more particularly to an ablation catheter having a temperature-controlled anchor element and related methods of use. As representative of one aspect of the present disclosure, FIGS. 1A-C illustrate a dual-energy catheter that 10 combines temperature-controlled anchor ("cryo-anchoring") and ablation (e.g., radiofrequency or RF ablation) elements to achieve controlled tissue ablation in dynamic mechanical environments (e.g., in vivo). Using the catheter 10 described herein, the present disclosure is based, at least in part, on the discovery that: (1) RF energy with cryo-anchoring reduced the determinant of the deformation gradient tensor at systolic loading; (2) infrared imaging revealed distinct regions of cryo-anchoring and tissue ablation, demonstrating that cryo-anchoring and ablation modalities do not counteract one another; and (3) cryogenic anchor strength to tissue was reduced but still robust during the application of RF energy. Based at least in part on this discovery, the present disclosure provides temperature-controlled anchor and ablation elements that can function simultaneously in close proximity on a single catheter tip to effectively improve physiological functioning of a target tissue, such as a dysfunctional mitral valve leaflet.

One aspect of the present disclosure is illustrated in FIGS. 1A-B and includes a catheter 10 for ablating tissue (e.g., cardiac tissue). The catheter 10 comprises a catheter body 12, a temperature-controlled anchor element 14 that is operably coupled to the catheter body, and an ablation element 16 that is axially spaced apart from the anchor element and operably coupled to the catheter body. Advantageously, the spaced apart relationship between the anchor element 14 and the ablation element 16 provides better tissue anchoring and more precise delivery of ablation energy to a target tissue. The spaced apart configuration of the anchor and ablation elements 14 and 16 is unlike conventional catheters, such as the cryoablation catheter disclosed in U.S. Pat. No. 7,465,300 to Arless et al. (hereinafter, "the '300 patent"), which includes a cooling tip that also serves as an RF tip electrode. Since the same tip is used to cool and heat target tissue, the tip of the catheter cannot simultaneously be used for cryo-anchoring and ablation, as can be done by the catheter 10 of the present disclosure. Consequently, highly accurate and precise delivery of ablation energy to a target tissue (as compared to the present disclosure) is not possible using conventional cryoablation catheters.

In some instances, the catheter body 12 has an elongated, generally cylindrical configuration with a distal end portion 18 oppositely disposed from a proximal end portion 20. The catheter body 12 includes an outer surface 22 (FIG. 1B) and an oppositely disposed inner surface 24. The outer and inner surfaces 22 and 24 of the catheter body 12 define a catheter wall 26 that can have any desired thickness. The inner surface 24 of the catheter body 12 defines a cavity, which houses a cooling mechanism 28 (described below). The outside diameter of the catheter body 12 can vary depending upon the intended application of the catheter 10. In some instances, the outside diameter of the catheter body 12 can be 3 Fr to 8 Fr or more. In one example, the outside diameter of the catheter body 12 can be 4 Fr.

The catheter body 12 can have a rigid, semi-rigid, or flexible configuration depending upon its intended application. In some instances, the catheter body 12 can be made of one or a combination of flexible biocompatible materials, such as polyurethane. The biocompatible material(s) used to form the catheter body 12 can impart the catheter 10 with sufficient strength while maintaining the flexibility required to maneuver the catheter through the vascular system of a subject. In some instances, different portions or regions of the catheter body 12 can be made of different materials to impart each of the portions or regions with a desired flexibility. In other instances, the catheter body 12 may be configured for controlled deflection. For example, the catheter body 12 can include a pull-wire (not shown) that can be manipulated (e.g., pulled) to cause the distal end portion 18 of the catheter body to bend preferentially from a non-deflected position to a deflected position.

In another aspect, the catheter body 12 includes a first portion 30 having at least one temperature-controlled anchor element 14 thereon. The anchor element 14 is configured to attach the distal end portion 18 of the catheter body 12 to tissue by forming a congealed adherence layer between the anchor element and the tissue. For example, the anchor element 14 can anchor the catheter 10 to tissue using a temperature-controlled surface to form a congealed adherence layer, such as a solid ice or frozen layer that is formed from tissue and/or fluids adjacent the tissue. In some instances, the anchor element 14 can be configured to provide a cryogenically-cooled surface at a temperature that is higher than the temperature used to cryogenically ablate tissue, but sufficiently cool so as to form a frozen or congealed adherence layer to anchor the catheter 10 to the tissue. This is similar to "cryo-mapping" technologies where cryogenic temperatures as low as −30° C. are used but do not cause permanent thermal damage. Permanent thermal damage occurs at −80° C. for extended times. "Cryo-anchoring" is also different from cryoablation because, to perform sufficient cryoablation, freeze-thaw cycles must be repeated over several cycles such that ice crystals form and rupture cell membranes. "Cryo-anchoring" of the present disclosure, however, entails neither rupturing of cell membranes nor freeze-thaw cycling.

The anchor element 14 can include a structure (or structures) for cooling a catheter surface that is/are similar to cryogenic catheter ablation tips used to cryogenically ablate tissue, such as those disclosed in the '300 patent. The anchor element 14 can be made of one or more biocompatible materials (e.g., copper, stainless steel, or the like) capable of providing a cryogenically-cooled surface. The anchor element 14 can be sized and configured depending upon the intended application of the catheter 10. In one example, the anchor element 14 can comprise a U-shaped distal tip that is securely mated to a portion of the catheter body 12. In another example, the anchor element 14 can have a length of about 1 mm to about 3 mm, such as about 1.9 mm. Although the anchor element 14 is shown in FIG. 1A as being distal to the ablation element 16, it will be appreciated that the location of the anchor element relative to the ablation element can be switched such that the ablation element is located distal to the anchor element.

In another aspect, the catheter 10 includes a second portion 32 having at least one ablation element 16 thereon. The first portion 30 (e.g., the anchor element 14) and the second portion 32 (e.g., the ablation element 16) are axially spaced apart and separated from each other by an insulating portion 34.

The insulating portion 34 can be configured to resist, mitigate, or prevent energy transfer between the first portion 30 (e.g., the anchor element 14) and the second portion 32 (e.g., the ablation element 16). For example, the insulating portion 34 can be configured to resist, mitigate, or prevent heat transfer from the ablation element 16 to the anchor element 14 during operation of the catheter 10. The width W of the insulating portion 34, and thus the distance between the anchor element 14 and the ablation element 16, can be varied as needed. In one example, the width W can be about 1 mm. The insulating portion 34 can be formed from the same material(s) as the material(s) used to form the catheter body 12. Where the catheter body 12 is formed from polyurethane, for example, the insulating portion 34 can also be formed from polyurethane. In other instances, the insulating portion 34 can be formed from a different material (or materials) used to form the catheter body 12.

In another aspect, the ablation element 16 can be securely connected to, or disposed on, the catheter body 12 at the second portion 32. As described in more detail below, the ablation element 16 is configured to ablate tissue when the anchor element is attached to the tissue. The ablation element 16 can be a RF ablation element (e.g., RF electrode); however, any suitable ablation element can be used, including microwave energy, laser energy, heat energy and/or a cryogenically-cooled ablation element. It will be appreciated that any number of ablation elements 16 can be included as part of the catheter 10, so long as each of the ablation elements is axially spaced apart from the anchor element 14. In one example, the ablation element 16 can include a cylindrical electrode that is securely disposed about the entire outer diameter (e.g., 360°) of the second portion 32. In another example, the ablation element 16 can comprise an RF electrode having a length of about 1 mm to about 3 mm, such as about 1.9 mm.

Figure 2A:
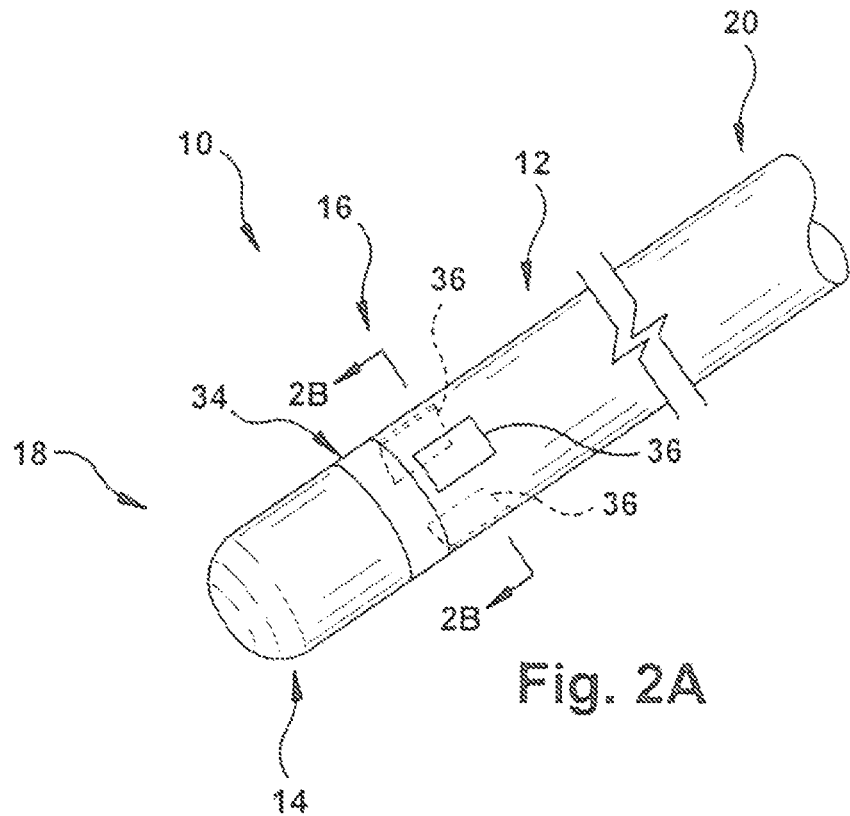
FIG. 2A is a perspective view showing an alternative configuration of the catheter in FIG. 1A.
Figure 2B:
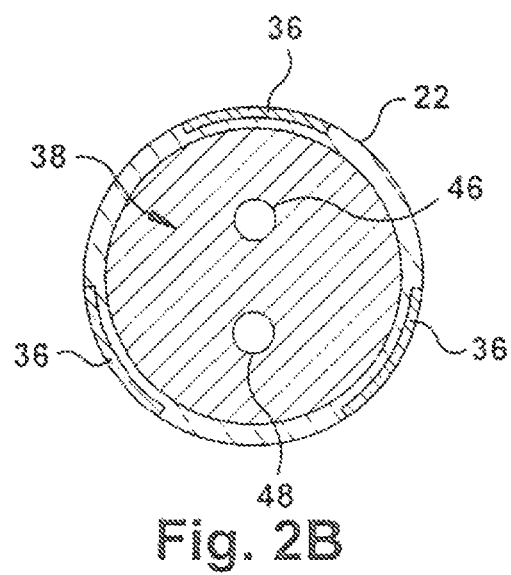
FIG. 2B is a cross-sectional view taken along Line 2B-2B in FIG. 2A.

In another aspect, the ablation element 16 can be configured to allow for more direct energy delivery to the tissue and thereby decrease the amount of energy lost to the blood stream. As shown in FIGS. 2A-B, the ablation element 16 can include three separate RF electrodes 36, each of which comprises approximately 120° of the outer diameter of the second portion 32. In some instances, each of the RF electrodes 36 can be insulated from one another. In other instances, each of the RF electrodes 36 can be radially-aligned with the other RF electrodes. By including three separate electrodes 36, RF energy can be delivered to the electrode(s) in direct contact with the tissue, thereby ensuring that the majority of RF energy enters the tissue and not the bloodstream.

Figure 3A:
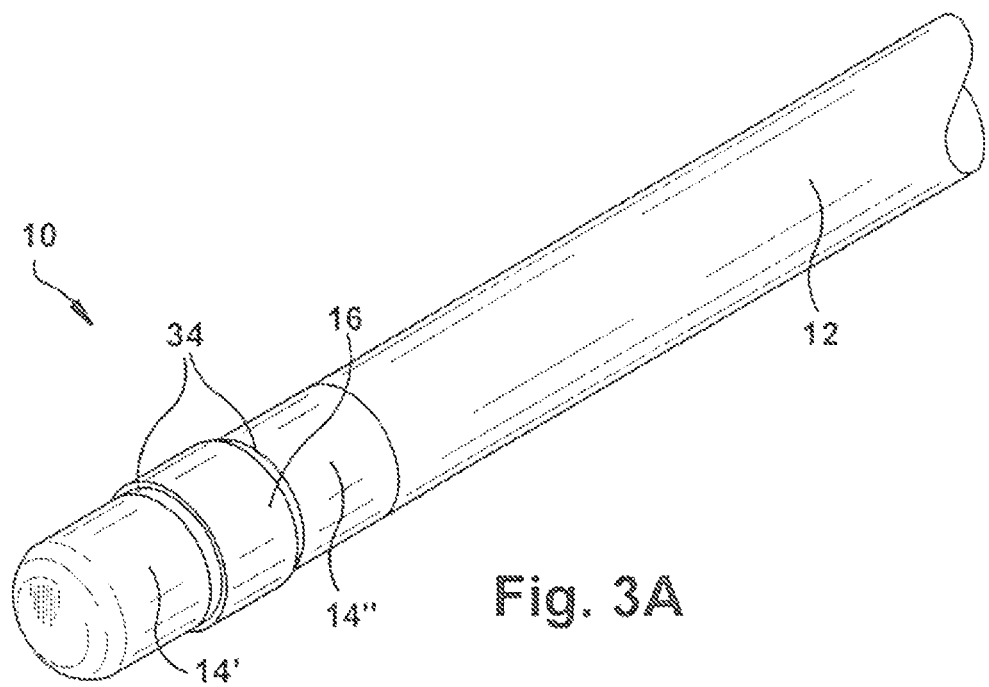
FIG. 3A is a perspective view showing an alternative configuration of the catheter in FIG. 1A.
Figure 3B:
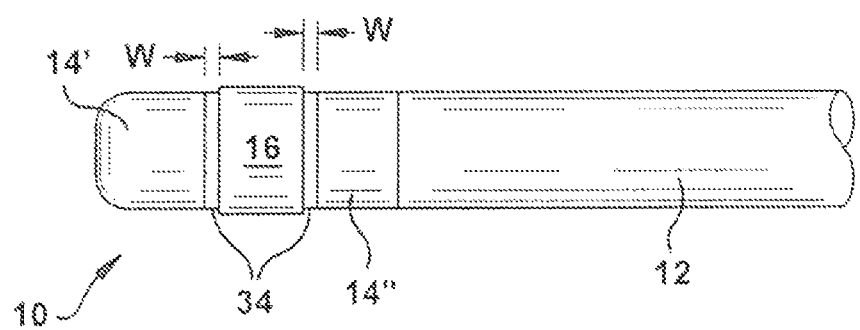
FIG. 3B is a side view of the catheter in FIG. 3A.

In another aspect, the catheter 10 can be configured as shown in FIGS. 3A-B. For example, the catheter 10 can include a first anchor element 14', an ablation element 16, and a second anchor element 14". Each of the first anchor element 14', the ablation element 16, and the second anchor element 14" can be axially spaced apart from one another. In some instances, the first and second anchor elements 14' and 14" can be axially spaced apart from the ablation element 16 by separate insulating portions 34. The width W of each insulating portion 34 can be varied as needed. For example, the width W of each of the insulating portions 34 can be equal to one another or, alternatively, different than the other. Advantageously, locating the ablation element 16 between the first and second anchor elements 14' and 14" ensures that both anchor elements, and therefore the ablation element, adhere to the target tissue during operation of the catheter 10. Consequently, the improved cryo-anchoring provides more precise delivery of ablation energy to the target tissue.

In another aspect, the catheter body 12 includes a cooling mechanism 28 configured to convey or circulate a cryogenically-cooled fluid (e.g., liquid nitrogen) therethrough. The cooling mechanism 28 can be housed within the cavity, which is defined by the inner surface 24 of the catheter body 12. A portion of the cavity can be partitioned by a sealing member 38, which forms a cooling chamber 40 for receiving an amount of the cryogenically-cooled fluid. As discussed below, the cooling mechanism 28 can further include first and second fluid conduits 42 and 44 for conveying a cryogenically-cooled fluid into and out of the cooling chamber 40 (respectively). By circulating the cryogenically-cooled fluid in the cooling chamber 40, the anchor element 14 can be configured to provide a cryogenically-cooled surface.

As shown in FIG. 1B, the sealing member 38 can be radially-aligned with the insulating portion 34 of the catheter body 12. The sealing member 38 can be configured similar to a rubber stopper, i.e., capable of preventing fluid flow between oppositely disposed spaces or cavities. In some instances, the sealing member 38 can be dimensioned and sized to sealingly conform to a portion of the inner surface 24 of the catheter body 12. For example, the sealing member 38 can have a substantially circular shape that mirrors the circular cross-sectional profile of the catheter body 12. The sealing member 38 can further include first and second channels 46 and 48 (FIG. 1C) that extend axially therethrough. The first and second channels 46 and 48 are configured to sealingly receive the first and second fluid conduits 42 and 44 (respectively) (FIG. 1B). The first and second channels 46 and 48 can be radially aligned with one another as shown in FIG. 1C; however, it will be appreciated that other configurations are possible.

Figure 4:
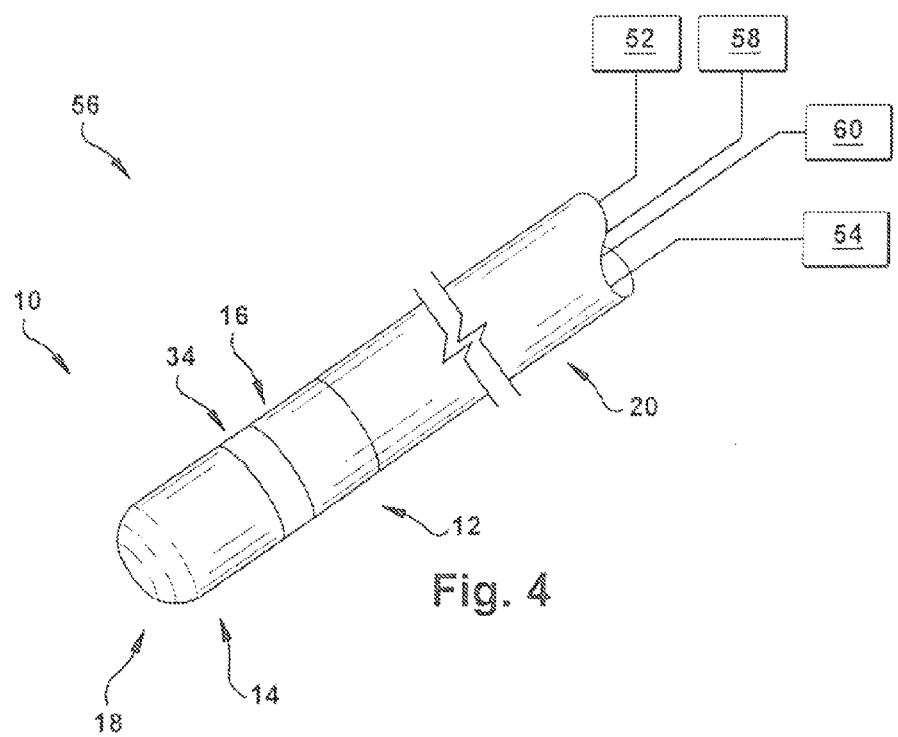
FIG. 4 is a schematic illustration showing a catheter system for ablating tissue constructed in accordance with another aspect of the present disclosure.

Referring to FIG. 1B, each of the first and second fluid conduits 42 and 44 can comprise an elongated, hollow tube that extends through the cavity of the catheter body 12. Each of the first and second fluid conduits 42 and 44 includes an open distal end 50, which is in fluid communication with the cooling chamber 40 so that a cryogenically-cooled fluid can flow therethrough. In some instances, the first fluid conduit 42 is configured to flow a cryogenically-cooled fluid from a cryogenically-cooled fluid source 52 (FIG. 4) into the cooling chamber 40 (FIG. 1B). In such instances, a proximal end (not shown) of the first fluid conduit 42 can be fluidly connected to the cryogenically-cooled fluid source 52 (FIG. 4). In other instances, the second fluid conduit 44 (FIG. 1B) is configured to flow a cryogenically-cooled fluid from the cooling chamber 40 towards a vacuum source 54 (FIG. 4). In such instances, a proximal end (not shown) of the second fluid conduit 44 (FIG. 1B) can be fluidly connected to the vacuum source 54 (FIG. 4). It will be appreciated that the cooling mechanism 28 (FIG. 1B) can include any number of fluid conduits sufficient to circulate a cryogenically-cooled fluid in the cooling chamber 40 and thereby provide a cryogenically-cooled surface.

In another aspect, a catheter system 56 is illustrated in FIG. 4. In some instances, the catheter system 56 can include a catheter 10 for ablating tissue, a cryogenically-cooled fluid source 52, a vacuum source 54, a power source 58, and a controller 60. The cryogenically-cooled fluid source 52 can include any vessel or container capable of serving as a reservoir for the cryogenically-cooled fluid. In one example, the cryogenically-cooled fluid source 52 can comprise a handheld canister (not shown). The cryogenically-cooled fluid source 52 can be operated manually or automatically. The vacuum source 54 can include any suitable pump or similar device capable of manually or automatically providing a vacuum to flow a cryogenically-cooled fluid from the cooling chamber 40 through the second fluid conduit 44. The power source 58 can be in electrical communication with the ablation element 16, and include any device capable of providing energy thereto. In one example, the power source 58 can include an RF generator capable of delivering an electrical signal of about 500 kHz at a power of up to about 50 W.

The controller 60 can be configured to control one or more components of the catheter system 56. In some instances, the controller 60 can include an anchor control module (not shown) configured to control the anchor element 14. For example, the amount of the cryogenically-cooled fluid and/or the temperature of the anchor element 14 can be controlled by the anchor control module. Thus, the controller 60 can be in electrical communication with the cryogenically-cooled fluid source 52 and the vacuum source 54. In other instances, the controller 60 can include an ablation control module configured to control the ablation element 16. For example, the temperature of the ablation element 16 can be controlled by the ablation control module. Thus, the controller 60 can be in electrical communication with the power source 58.

The controller 60 can be configured to coordinate operation of one or more components of the catheter system 56. In some instances, the controller 60 can include circuitry (e.g., a microprocessor, memory, etc.) and software (e.g., one or more algorithms) in electrical communication with the component(s) of the catheter system 56. In some instances, the controller 60 (e.g., the software) can pre-programmed to selectively control the temperature of the ablation element 16 and/or the anchor element 14. Alternatively, where the catheter 10 includes a sensor (e.g., a temperature sensor) (not shown), the controller 60 can selectively control the temperature of the ablation element 16 and/or the anchor element 14 based on detected tissue temperature levels. The controller 60 can be powered by a power source (not shown), such as a battery.

Figure 5:
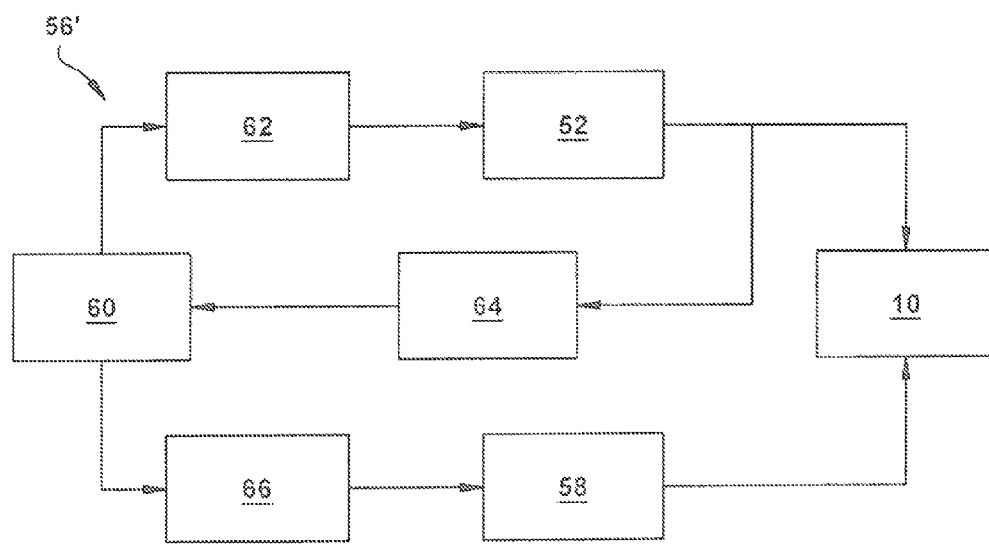
FIG. 5 is a schematic illustration showing an alternative configuration of the catheter system in FIG. 4.

One example of a catheter system 56 is illustrated in FIG. 5. The catheter system 56' can include the following components: a catheter 10 for ablating tissue; a controller 60; a servo 62; a cryogenically-cooled fluid source 52; a thermocouple 64; a power source 58; and a solenoid valve 66. In some instances, the controller 60 can be in electrical communication with each of the components of the system 56'. In one example, the catheter 10 can be configured in a similar or identical manner as the catheter illustrated in FIGS. 1A-C. In some instances, the servo 62 can be configured to modulate flow of the cryogenically-cooled fluid source 52 (e.g., on and off). In other instances, the cryogenically-cooled fluid source 52 can include a canister of liquid nitrogen. In further instances, the thermocouple 64 can be operably connected to any portion of cooling mechanism 28 and/or the anchor element 14. In one example, the power source 58 can include an RF generator. In another example, the solenoid valve 66 can be configured to control air flow.

Figure 6:
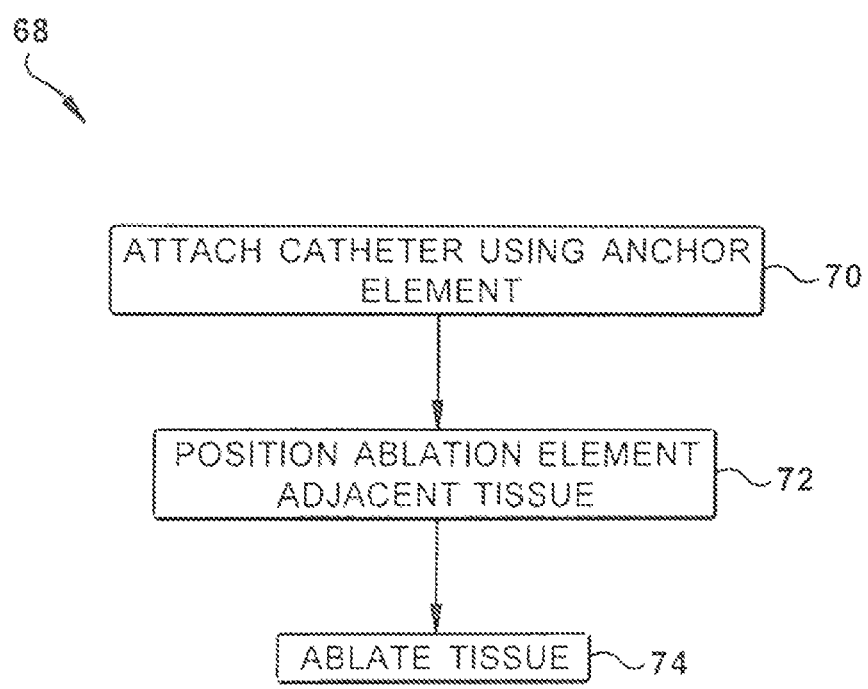
FIG. 6 is a process flow diagram illustrating a method for ablating tissue according to another aspect of the present disclosure.

Another aspect of the present disclosure is illustrated in FIG. 6 and includes a method 68 for ablating tissue in a subject. Although the method 68 is described below in terms of treating mitral valve disease or malfunction (e.g., mitral valve prolapse), it will be appreciated that the method may also be useful for any percutaneous procedure where anchored ablation would provide more precise spatial control. For example, the method 68 may find use in treatments that require the use of RF ablation in dynamic environments, such as treatment of cardiac arrhythmias.

Mitral valve prolapse is one subtype of mitral valve disease, which is often characterized by enlarged leaflets that are thickened and have disrupted collagen architecture. The increased surface of myxomatous leaflets with mitral valve prolapse leads to mitral regurgitation. Due to the complications associated with open-chest surgery, there is a need for percutaneous treatment options; however, any device that aims to percutaneously treat mitral valve prolapse must do so in a highly dynamic mechanical environment. Additionally, due to the high rate of blood flow across the mitral valve and the resulting potential for heat convection, application of energy (e.g., RF energy) to the target tissue (e.g., mitral leaflet(s)) should be performed with an electrode (or electrodes) in direct contact with the target tissue.

As described in more detail below, the present disclosure provides a method 68 for maintaining direct catheter contact with a moving target tissue, such as mitral valve leaflet to enhance stability during a percutaneous treatment procedure. Utilizing a temperature-controlled anchor element 14, the catheter 10 of the present disclosure can effectively adhere to and alter mitral valve leaflet geometry and compliance, thereby reducing mitral valve leaflet size at maximum systolic load. Consequently, the method 68 can preserve the mitral valve apparatus and restore normal fluid mechanics.

Figure 7:
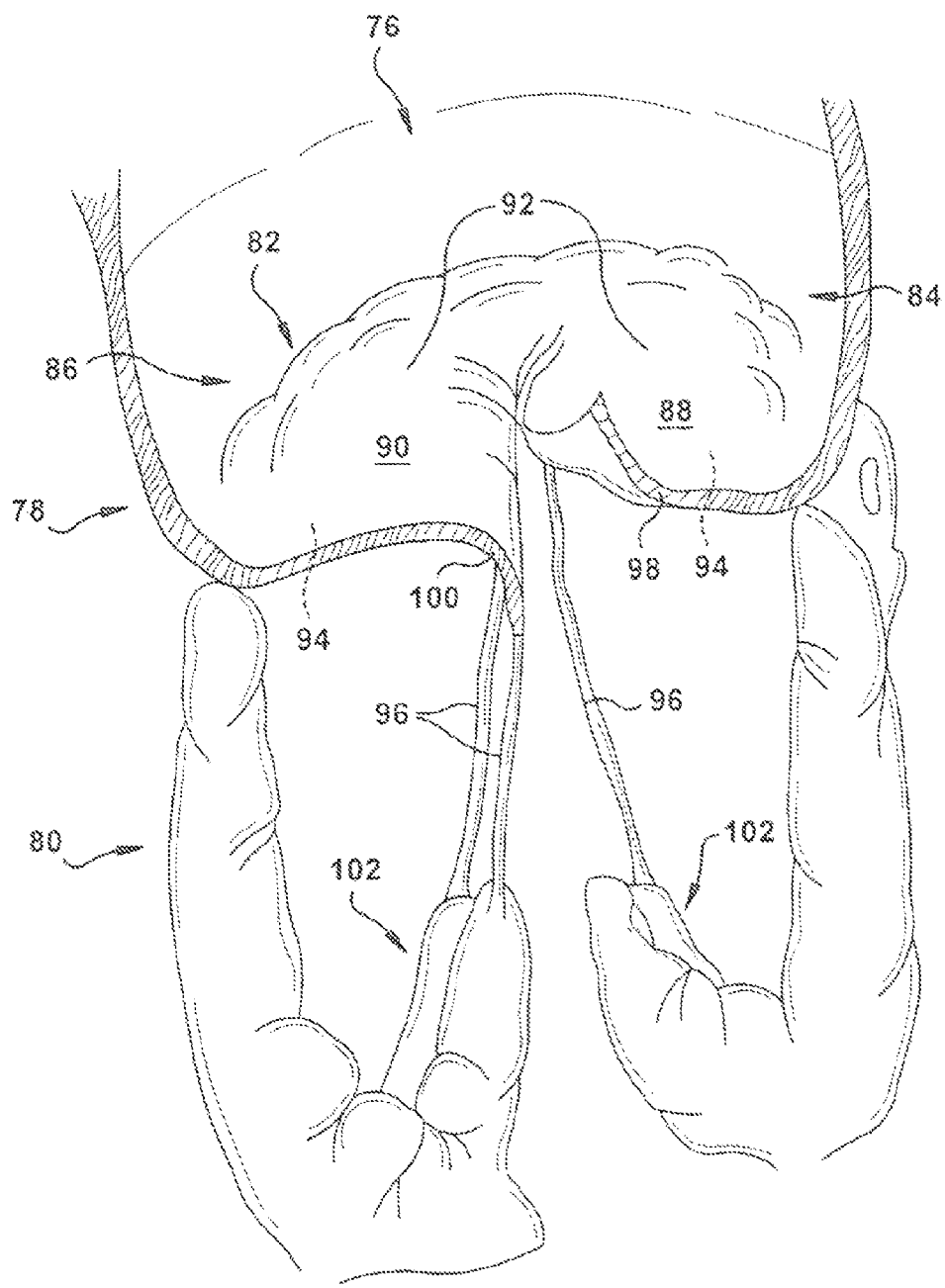
FIG. 7 is a cross-sectional view showing the left side of a human heart with a prolapsed mitral valve leaflet.

The mitral valve 76 (FIG. 7) is located between the left atrium 78 and the left ventricle 80, and functions to prevent the backflow of blood from the left ventricle into the left atrium during contraction. The mitral valve 76 has a D-shaped annulus 82 that defines the opening between the left atrium 78 and the left ventricle 80, and includes oppositely disposed anterior and posterior portions 84 and 86. The mitral valve 76 is formed by two leaflets; namely, the anterior leaflet 88 and the posterior leaflet 90, each of which includes oppositely disposed superior and inferior surfaces 92 and 94. The anterior leaflet 88 extends along the generally planar base of the D-shaped valve annulus 82 between two fibrous trigones (not shown). The posterior leaflet 86 extends arcuately around the curved portion of the D-shaped annulus 82 of the mitral valve 76. Chordae tendineae 96 respectively extend between the inferior free edge 98 of the anterior mitral leaflet 88 and the inferior free edge 100 of the posterior mitral leaflet 90 to the papillary muscles 102 in the left ventricle 80. In the case of mitral valve prolapse (shown in FIG. 7), the anterior mitral leaflet 88 can bulge into the left atrium 78 during contraction of the heart, thereby allowing blood to leak back into the left ventricle 80 (regurgitation).

Figure 8:
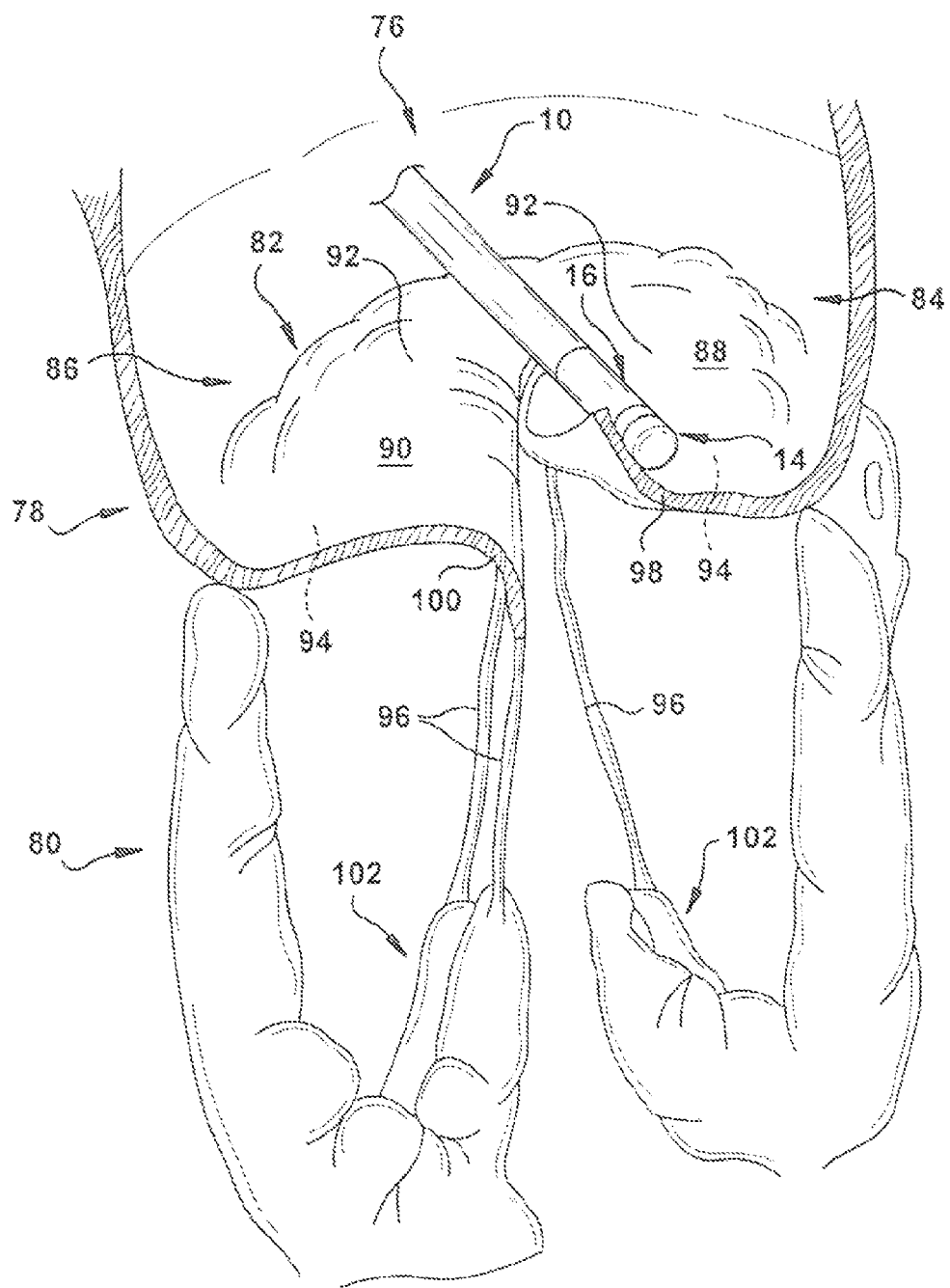
FIG. 8 is a cross-sectional view showing a temperature-controlled anchor element and an ablation element of the catheter (FIGS. 1A-C) in direct contact with the prolapsed mitral valve leaflet in FIG. 7.

To treat a prolapsed anterior mitral leaflet 88 in a subject, a catheter 10 is introduced into the vasculature of the subject using a known percutaneous surgical technique. For example, access to the prolapsed mitral leaflet 88 can be obtained via a trans-septal approach. At Step 70, the distal end portion 18 of the catheter 10 is placed into direct contact with a portion of the anterior mitral leaflet 88 (FIG. 8). The anchor element 14 of the catheter 10 can be sized and configured to attach to a portion of the anterior mitral leaflet 88 of a beating heart, i.e., while the mitral valve 76 is moving with respect to the surrounding cardiac tissue. In some instances, the controller 60 can include a cardiac cycle monitor that uses the cardiac cycle to estimate the moving location of the mitral valve 76 during a cardiac cycle so that a medical health professional can move the anchor element 14 into position on the prolapsed mitral leaflet 88.

Either before, during, or after contacting the anchor element 14 with a portion of the prolapsed mitral leaflet 88, the cooling mechanism 28 can be activated to cool the anchor element. In one example, the cooling mechanism 28 can be activated to cool the anchor element 14 to a temperature between about −90° C. and about −30° C. Consequently, the cooled surface of the anchor element 14 can connect the first portion 30 (e.g., anchor element) of the catheter 10 to the anterior mitral leaflet 88 of a beating heart such that the first portion 30 moves together with the mitral valve 76.

At Step 72, the second portion 32 (e.g., ablation element 16) of the catheter 10 is positioned adjacent the anterior mitral leaflet 88 while the mitral valve 76 continues to function during the cardiac cycle. Thus, ablation of mitral leaflet tissue can be performed percutaneously while the mitral valve 76 is moving with respect to the surrounding cardiac tissue without substantial disruption to cardiac function. In one example, and without wishing to be bound by any particular theory, the ablation element 16 can deliver ablation energy (e.g., RF energy) for a time and at a temperature sufficient to coagulate the collagen of at least a portion of the anterior mitral leaflet 88 (Step 74). In some instances, the amount of energy (J) delivered to the leaflet tissue can vary depending upon the severity of mitral valve dysfunction, the location of the diseased or dysfunctional mitral tissue, the overall health of the subject, etc. For example, a desired amount of power (W), such as about 20 W to about 100 W or more can be delivered to the mitral leaflet tissue for a desired period of time (e.g., about 5 seconds to about 60 seconds or more).

Figure 9:
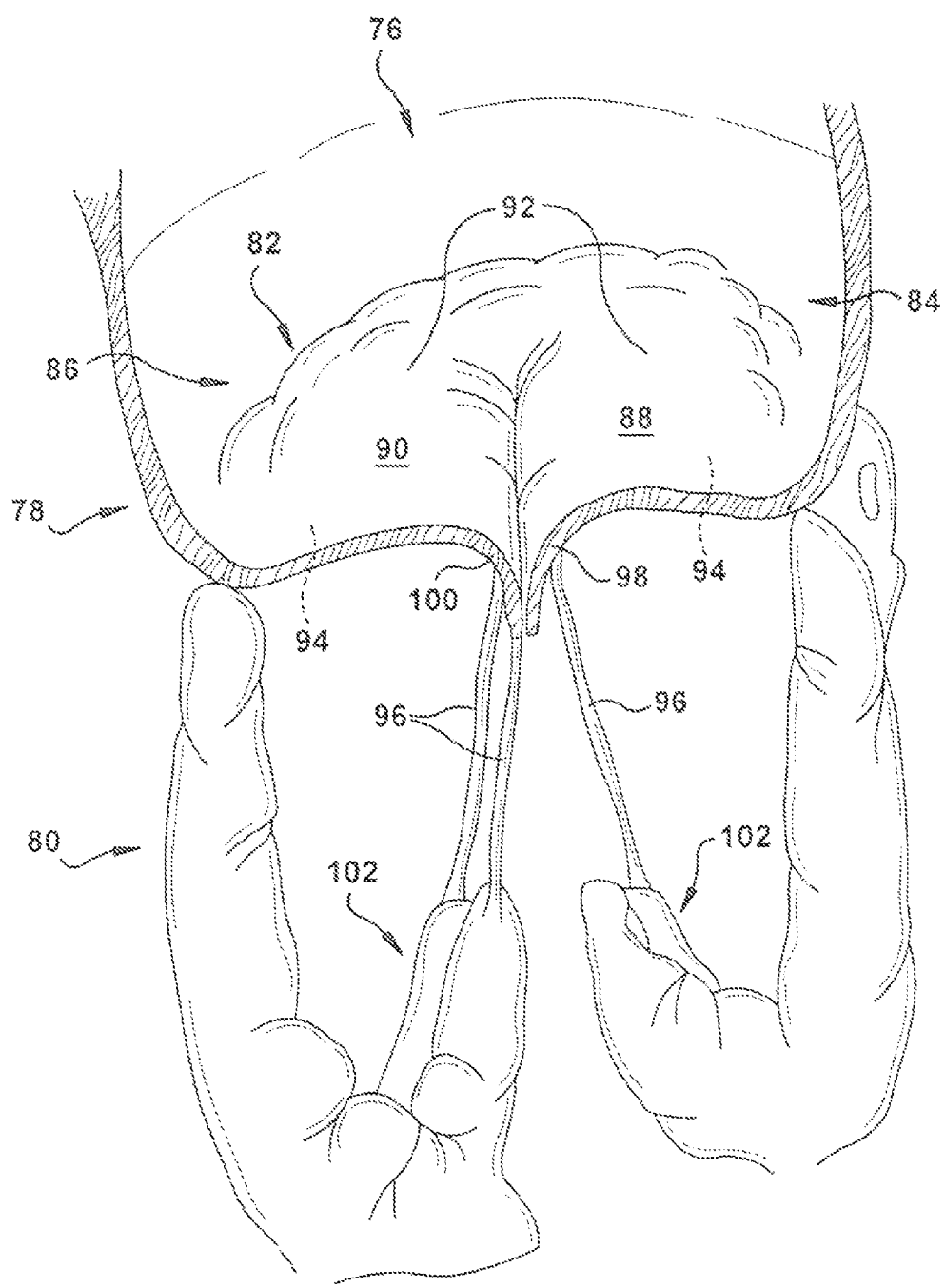
FIG. 9 is a cross-sectional view showing the mitral valve in FIG. 8 following treatment with the catheter.

Upon delivering an amount of energy to the mitral leaflet tissue, the coagulated collagen can alter the intrinsic stiffness of the mitral valve 76 and thereby remodel the mitral apparatus (FIG. 9). By altering the intrinsic stiffness of the mitral valve 76, cardiac function can be improved without requiring invasive surgeries for mitral valve repair or replacement. Advantageously, the present disclosure provides a method 68 for effectively altering (e.g., reducing) mitral valve leaflet geometry and compliance at maximum systolic load. Consequently, the method 68 can preserve the mitral valve apparatus and restore normal fluid mechanics.

From the above description, those skilled in the art will perceive improvements, changes and modifications. Such improvements, changes, and modifications are within the skill of one in the art and are intended to be covered by the appended claims. All references cited herein and listed above are incorporated by reference in their entireties as needed and as discussed herein.

The following is claimed:

1. A catheter comprising:
    a catheter body having a temperature-controlled anchor element thereon that is configured to attach said catheter body to tissue by forming a congealed adherence layer between said anchor element and the tissue; and
    a radio frequency (RF) ablation element connected to said catheter body and being axially spaced apart from said anchor element, said ablation element configured to ablate tissue when said anchor element is attached to the tissue;
    wherein said anchor element and said RF ablation element are separated from each other by an insulating portion that surrounds said catheter body and resists heat transfer from said RF ablation element to said anchor element during operation of said catheter.

2. The catheter of claim 1, wherein said catheter body comprises a first portion having said anchor element thereon and a second portion having said ablation element thereon, said first and second portions being separated by an insulating portion.

3. The catheter of claim 1, wherein said catheter body further includes a cooling mechanism configured to convey a cryogenically-cooled fluid therethrough.

4. The catheter of claim 1, wherein said anchor element is configured to be cooled to a temperature between about −90° C. and out −30° C.

5. The catheter of claim 3, wherein said cooling mechanism further comprises a cryogenically-cooled fluid source configured to cool at least a portion of said anchor element.

6. The catheter of claim 1, wherein said anchor element is configured to attach said catheter body to tissue when the tissue is moving relative to said catheter body.

7. The catheter of claim 1, wherein said RF ablation element comprises a cylindrical electrode having an inner surface that surrounds, and is directly disposed on, a portion of an outer surface of said catheter body.

8. The catheter of claim 1, wherein said ablation element comprises a plurality of spaced apart, radially aligned electrodes.

9. The catheter of claim 1, wherein said ablation element is configured to ablate tissue when the tissue is moving relative to said catheter body.

10. The catheter of claim 1, wherein said anchor element is spaced apart from said ablation element such that said anchor element maintains a temperature sufficiently cool to form the congealed adhesion layer and said ablation element maintains a temperature sufficient to ablate the tissue.

11. A catheter comprising:
    a catheter body having first and second temperature-controlled anchor elements thereon, each of said first and second anchor elements being configured to attach said catheter body to tissue by forming a congealed adherence layer between said first and second anchor elements and the tissue; and
    a RF ablation element connected to said catheter body and disposed between said first and second anchor elements, said ablation element configured to ablate tissue when said first and second anchor elements are attached to the tissue;
    wherein each of said first anchor element, said second anchor element, and said ablation element is axially spaced apart from one another;
    wherein said anchor element and said RF ablation element are separated from each other by an insulating portion that surrounds said catheter body and resists heat transfer from said RF ablation element to said anchor element during operation of said catheter.

12. The catheter of claim 11, wherein said catheter body further includes a cooling mechanism configured to convey a cryogenically-cooled fluid therethrough.

13. The catheter of claim 11, wherein said first and second anchor elements are configured to attach said catheter body to tissue when the tissue is moving relative to said catheter body.

14. The catheter of claim 11, wherein said ablation element comprises a plurality of spaced apart, radially aligned electrodes.

15. The catheter of claim 11, wherein said ablation element is configured to ablate tissue when the tissue is moving relative to said catheter body.

16. The catheter of claim 11, wherein said first and second anchor elements are spaced apart from said ablation element such that said first and second anchor elements maintain a temperature sufficiently cool to form the congealed adhesion layer and said ablation element maintains a temperature sufficient to ablate the tissue.

17. A method for ablating tissue, said method comprising the steps of:
    positioning a catheter body having a temperature-controlled anchor element thereon adjacent body tissue while cooling the anchor element to a temperature sufficient to form a congealed adherence layer between the anchor element and the tissue to attach the catheter body to the tissue;
    positioning a RF ablation element connected to the catheter body adjacent the tissue, the RF ablation element being axially spaced apart from the anchor element, the anchor element and the RF ablation element being separated from each other by an insulating portion that surrounds the catheter body and resists heat transfer from the RF ablation element to the anchor element during operation of the catheter; and ablating the tissue when the anchor element is attached to the tissue.

18. The method of claim 17, wherein the tissue comprises a mitral valve.

19. The method of claim 17, wherein the catheter is attached to the mitral valve in vivo when the mitral valve is moving.

20. The catheter of claim 1, wherein said insulating portion has a width such that said RF ablation element and said anchoring portion are in close proximity to one another.

* * * * *

UNITED STATES PATENT AND TRADEMARK OFFICE
CERTIFICATE OF CORRECTION

PATENT NO. : 9,259,261 B2  
APPLICATION NO. : 13/861884  
DATED : February 16, 2016  
INVENTOR(S) : Steven M. Boronyak et al.

It is certified that error appears in the above-identified patent and that said Letters Patent is hereby corrected as shown below:

In the Claims

Column 11, claim 4, line 64 reads, "and out -30° C." Should read -- and about -30° C. --

Signed and Sealed this  
Third Day of May, 2016

Michelle K. Lee  
*Director of the United States Patent and Trademark Office*